(12) United States Patent
Dilger et al.

(10) Patent No.: US 6,796,324 B2
(45) Date of Patent: Sep. 28, 2004

(54) FUGITIVE EMISSION COLLECTION DEVICE

(75) Inventors: John Patrick Dilger, Marshalltown, IA (US); Jerry Marvin Ceaser, Newton, IA (US)

(73) Assignee: Fisher Controls International, LLC, St. Louis, MO (US)

(*) Notice: Subject to any disclaimer, the term of this patent is extended or adjusted under 35 U.S.C. 154(b) by 158 days.

(21) Appl. No.: 09/997,028

(22) Filed: Nov. 28, 2001

(65) Prior Publication Data

US 2003/0098065 A1 May 29, 2003

(51) Int. Cl.⁷ ............................ G01M 3/18; G01N 1/14; F16K 41/04
(52) U.S. Cl. .................... 137/312; 73/46; 73/863.81; 73/864.73; 277/320; 277/512; 277/513; 277/522
(58) Field of Search ................. 73/46, 49.2, 49.8, 73/40.5 R, 40.7, 863.33, 863.81, 863.83, 864.34, 864.73; 137/312; 277/320, 520, 522, 530, 512, 513, 514; 285/93, 368

(56) References Cited

U.S. PATENT DOCUMENTS

| 3,141,685 A | | 7/1964 | Watts | |
|---|---|---|---|---|
| 3,307,574 A | * | 3/1967 | Anderson | 137/312 |
| 4,410,186 A | * | 10/1983 | Pierce, Jr. | 277/318 |
| 4,466,273 A | * | 8/1984 | Pillette | 73/46 |
| 4,573,344 A | | 3/1986 | Ezekoye | |
| 4,886,241 A | * | 12/1989 | Davis et al. | 251/214 |
| 4,888,979 A | * | 12/1989 | Steeper | 73/46 |
| 4,972,867 A | | 11/1990 | Ruesch | |
| 5,129,625 A | | 7/1992 | Wood et al. | 251/214 |
| 5,170,659 A | * | 12/1992 | Kemp | 73/46 |
| 5,182,076 A | * | 1/1993 | de Seroux et al. | 73/46 |
| 5,203,370 A | | 4/1993 | Block et al. | |
| 5,206,818 A | * | 4/1993 | Speranza | 73/40.5 R |
| 5,330,720 A | * | 7/1994 | Sorbo et al. | 73/46 |
| 5,345,812 A | * | 9/1994 | Haboian | 137/312 |
| 5,372,352 A | * | 12/1994 | Smith et al. | 251/214 |
| RE34,923 E | * | 5/1995 | Ruesch | 73/46 |
| 5,503,367 A | * | 4/1996 | Thompson et al. | 251/214 |
| 5,593,166 A | * | 1/1997 | Lovell et al. | 277/522 |
| 5,610,324 A | * | 3/1997 | Lawson | 73/46 |
| 5,921,552 A | | 7/1999 | Trackwell et al. | |
| 6,029,506 A | | 2/2000 | Dilger | 73/46 |
| 6,041,645 A | * | 3/2000 | Lawson et al. | 73/46 |
| 6,299,216 B1 | * | 10/2001 | Thompson | 285/93 |
| 6,553,810 B2 | * | 4/2003 | Webb et al. | 73/46 |

OTHER PUBLICATIONS

Copy of International Search Report for International Application No. PCT/US02/31921, dated Jan. 28, 2003, 7 pages.

* cited by examiner

Primary Examiner—George L. Walton
(74) Attorney, Agent, or Firm—Marshall, Gerstein & Borun LLP

(57) ABSTRACT

A fugitive emission collection device for acquiring an atmosphere sample around a seal is provided. The emission collection device has a rigid member that forms a low impedance cavity shaped to overlay a seal. The emission collection device has a conduit with an inlet in fluid communications with the low impedance cavity and an outlet that can be connected to a chemical sensing system to analyze the atmosphere sample for emissions leaking from the seal.

17 Claims, 2 Drawing Sheets

FUGITIVE EMISSION COLLECTION DEVICE

CROSS-REFERENCE TO RELATED U.S. PATENTS

This application is related to U.S. Pat. No. 6,029,506, filed on Nov. 12, 1997, entitled "Sample Retrieval System", and U.S. Pat. No. 5,129,625 filed on Oct. 9, 1990, entitled "Live Loaded Packing System", and is assigned to the same assignee as the present patent application, and the above referenced patents are hereby incorporated by reference.

FIELD OF INVENTION

The present invention relates generally to an emissions preservation and collection device. More specifically, the present invention relates to a device for acquiring an accurate sample of emissions in the atmosphere surrounding a seal.

BACKGROUND OF INVENTION

Plants and factories utilize process control devices to control the flow of fluids in processes. Process control valves are used to manufacture consumer articles or goods such as fuel, food, and clothes. Even a medium sized factory may utilize hundreds of control valves and dozens of pumps. Most industrial plants utilize volatile organic compounds (VOC's) in the processes that produce consumer goods. Nearly all industrial plants experience unwanted emissions of VOCs into the atmosphere. The emissions often escape from unintended sources such as valves, pumps, and plumbing involved in the process stream. Emissions from unintended sources are often referred to as "fugitive emissions." The material being controlled in a process will be referred to herein as a fluid although it may be a gas or a multi-phase media.

Many process control devices have shafts that are rotated to control a parameter of the process. For example, a control valve controls the flow of fluid by changing the position of a valve stem which moves a plug. The valve stem may slide up and down, or it may rotate to change the position of the plug. The valve stem travels in relation to a seal. The seal prevents the process fluid from escaping into the atmosphere or outside world.

In operation, a valve stem may move in relation to its valve seal as frequently as two times per second. In extreme cases the stem may move in relation to the seal as many as fifty times per second. Frequent movement of the valve stem and demanding service conditions such as large temperature fluctuations, harsh process chemicals and abrasive particles near the sealing surfaces accelerate the deterioration of the valve stem seal. Recent improvements in seal material and seal retention has greatly increased the service life of valve stem seals; however, eventually all valve seals deteriorate and leak process fluids into the environment. Thus, the monitoring of control valve seals for leakage has become a concern.

Other process control devices such as pumps also have rotating shafts. Thus, it is common for a seal around a pump shaft to develop a leak. Another sealing arrangement commonly occurring in a factory is a pipe flange or a flexible pipe coupling. Vibration in the piping, and seal deterioration due to age and exposure to elements also creates leaks in a process control system and correspondingly undesirable emissions.

In the past few years, the U.S. Government and foreign governments have become sensitive to the release of undesirable chemicals and compounds into the atmosphere. Correspondingly, the U.S. Government has continued to create and apply tougher standards for preventing the release of contaminants such as VOCs into the environment. The U.S. Environmental Protection Agency ("EPA") is the federal agency that is in charge of creating and enforcing the new legislation.

VOCs are very prevalent in industrial processes. Particularly, benzene, toluene, and 1,1,1-trichloroethane are three VOCs that are commonly utilized in manufacturing The EPA has promulgated regulations specifying the maximum permitted leakage of these VOCs from control valves and from factories generally. To comply with the regulations, a plant manager must create a factory audit procedure. The procedure will include recording VOC leakage measurements and reporting the measurements to the EPA.

To comply with one of the EPA regulations a factory must determine how many valves are leaking and the quantity of chemical being leaked by each valve. If an audit determines that the quantity of leaking valves and amount of VOCs released are under a predetermined limit, then according to the regulations, testing or surveys can be reduced in frequency. This is particularly important for large facilities that can contain, for example, 200,000 survey points. It becomes very costly to maintain a staff to constantly monitor 200,000 locations within a plant. Thus, accurate reporting of minimal leakage, significantly reduces the effort and expense for compliance with EPA regulations.

Because automated emission detection systems are not readily available, most factories are using portable instruments and conducting "walk through audits". A walk through audit requires physically visiting, measuring and recording emissions from survey points. This is very inefficient compared to an automated system which does not require a physical visit to the survey point.

In addition to the inefficiency of physically visiting and measuring emission, other problems plague such a system. For example, on a windy day, winds may blow the emission away and the portable measuring device will not detect an emission. Additionally, leakage may be dependent on the position of the valve stem. A worn, pitted or bent stem may not leak in one position but may have a severe leak in another position. A portable instrument takes one measurement while physically present, however an automated system can report emission 24 hours a day.

Portable instruments typically use a sampling probe to transport a small sample of the atmosphere, around the probe tip and adjacent to a small area on the seal, to sensors within the portable instrument. The procedural requirements for using a sample probe includes movement of the probe around the entire circumference of the seal and dwelling where the maximum leakage is detected. Thus, the measurement is made on a small portion of the seal and the "overall" leakage is not measured. Additionally, it can be difficult to circle the seal with the sample probe due obstructions such as the actuator frame or bonnet.

Currently automated fugitive emission sensing systems are not prevalent in process control systems. There are a few "make shift" or primitive installations. These are typically placed on valves subject to the most demanding service. Detection is important because immediate repair of leaking valves minimizes the required audits, and greatly reduces expenditures for EPA compliance. An additional benefit of an automated reporting system includes a more effective early warning system. The automated system can alert a facility operator to an impending seal failure. If the emission is flammable, toxic or hazardous, detection enables preventive measures to be taken before a dangerous situation arises.

There are two basic functions to any emission detection system. First, the system must acquire an accurate atmosphere sample by some sort of acquisition system and then it must process the sample to detect the concentration of the target chemical. It is critical that the acquisition system provide an uncontaminated, uniform and undiluted sample to be analyzed.

A permanent installation of an automated fugitive emission sensor system would minimize the "manual surveys" and usage of portable instruments and increase the accuracy of the measurements. However, permanently installed emission sensors also suffer from inaccurate sample acquisition systems. These installed emission sensors must also contend with sample preservation problems that may occur as a result of air turbulence. Thus, it is an object of the present invention to provide a device to effectively acquire an accurate sample of atmosphere adjacent to a seal, either for a portable instrument or an automated emission detection system to enable a chemical detection system to accurately measure emissions.

SUMMARY OF THE INVENTION

Accordingly, it is an object of this invention to provide a low cost and robust fugitive emission collection device;

It is another object of the present invention to provide a highly efficient collection mechanism for acquiring a uniform fugitive emission sample;

It is yet another object to provide a low impedance cavity for capturing a sample of atmosphere in close proximity to a seal and delivering the sample to a emission detection system to determine if fugitive emissions are present.

SUMMARY

A fugitive emission collection device for acquiring an atmosphere sample around a seal is provided. The emission collection device is a rigid member that forms a low impedance cavity shaped to overlay the seal. The emission collection device has a conduit having an inlet in fluid communication with the low impedance cavity and an outlet that can be connected to an emission detection system, which is used to analyze the atmosphere to determine if excess emissions are leaking from the seal. In the preferred embodiment the collection device is manufactured in two pieces, which basically consists of a base and a cover. The conduit can be created by initially forming a recess in the mating surface of either the base or the cover before they are assembled together. A more uniform and accurate sample of the atmosphere around a seal can be drawn from the low impedance cavity by a collection device that has multiple inlets equally spaced around and proximate to the seal.

BRIEF DESCRIPTION OF THE DRAWINGS

The features and advantages of the present invention will be best appreciated upon reference to the following detailed description and the accompanying drawings, in which.

DETAILED DESCRIPTION

The present invention provides an emission collection device for acquiring an accurate sample of the atmosphere around a seal so that it can be tested for emissions. The emission collection device is part of an overall emission detection system that is used to determine the emissions of a leaking seal.

Figure 1:
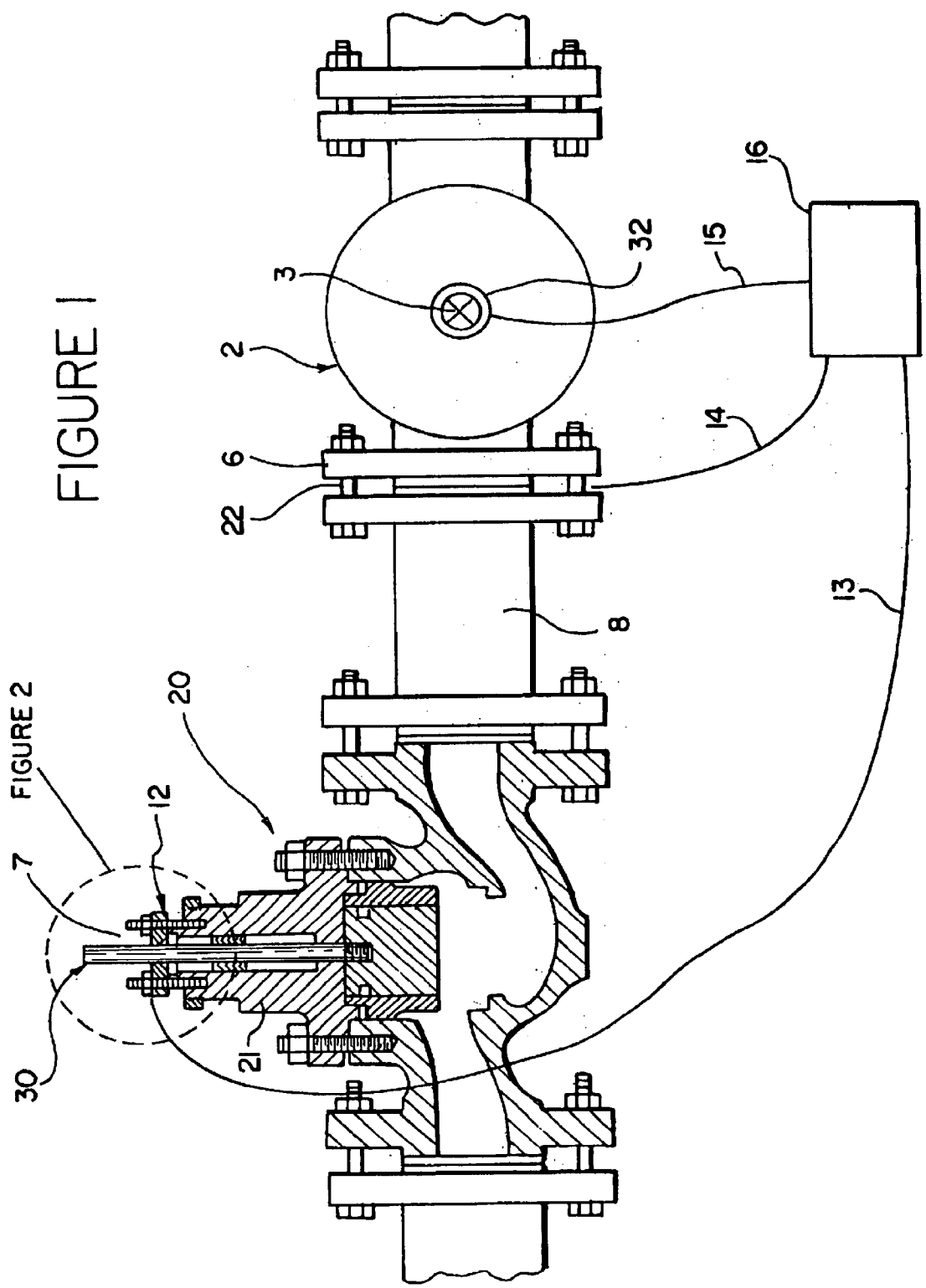
FIG. 1 depicts a portion of a process with emission collection devices integrated with process control devices and process piping.

Leaking seals may exist in a variety of process components such as a pump 2, process piping 8, pipe flanges 6, and a control valve 20. In accordance with the present invention, emission collection devices (ECDs) are assembled to each of the process components where emission leaks may be a concern. Three examples are shown in FIG. 1 wherein control valve 20 is illustrated in a cut-away view. A valve ECD 12 is placed around a stem 30 of a control valve 20 and secured to a bonnet 21. A pipe flange ECD 22 is shown assembled to pipe flange 6. The third example shows a pump shaft ECD 32 assembled to pump 2 so that it fits around a pump shaft 3. A chemical detection system 16 is used to pull atmosphere samples from the ECDs 12,22 and 32 via aspiration tubes 13, 14, and 15 to determine if unacceptable levels of fugitive emissions are present.

Chemical sensing detection system 16 is preferably of the type designed to detect extremely small concentrations of a target chemical in a sample provided by the ECDs. Sensitivities on the order of 10 parts per million are readily achievable for a standard chemical detection system In these extremely small concentrations, the emissions are generally in the gas phase. For these types of detection systems it is common to use an integrated sample retrieval system to remove gas from the critical area by suction. An example of a sample retrieval system is described in U.S. Pat. No. 6,029,506 and is hereby incorporated by reference.

Figure 2:
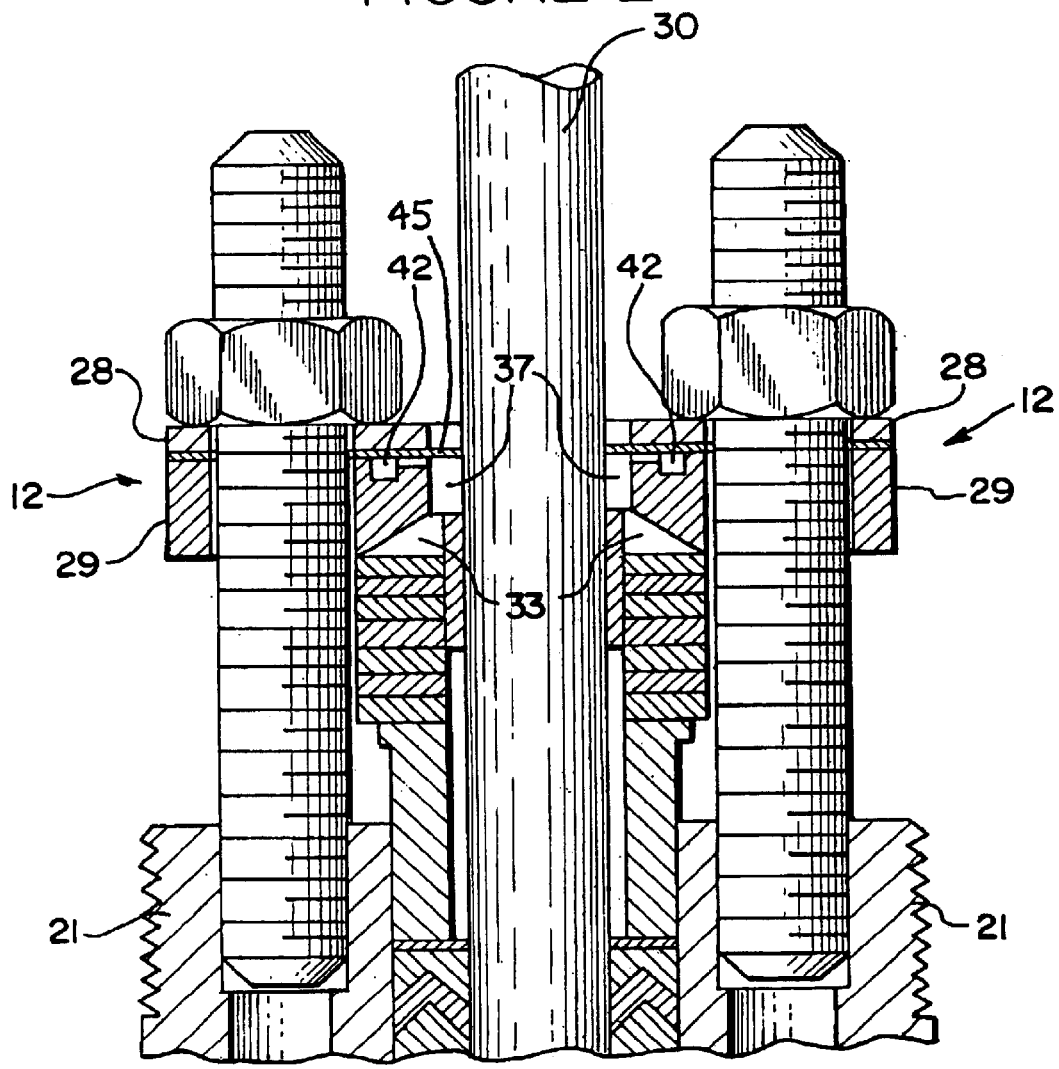
FIG. 2 is an enlarged, cut-away view of an emission collection device incorporated on a process control valve shown in FIG. 1 in accordance with the present invention.

Referring now to FIG. 2, a more detailed cut away view of encircled area 7 of FIG. 1 is shown to illustrate the concepts of the present invention. While the concept will be described in reference to the valve 20, it should be clear to one skilled in the art that the same concepts apply with respect to the pipe flange 6, the pump 2, or any other device where there is a concern of emissions leaking from a seal. As shown the valve ECD 12 primarily consists of a base 29 and a cover 28. The valve ECD 12 is mounted to the bonnet 21 and is used to form a low impedance cavity 37 around seal 33 and the valve stem 30.

Low impedance cavity 37 operates as a protective cavity that shields the atmosphere around the seal 33 from air turbulence or wind that may be present. This shield or windbreak helps to prevent inaccurate readings. It is important that emissions rise and escape the low impedance cavity 37 without undue interference. Thus the goal of the low impedance cavity is to preserve the natural flow of emissions from the sealing surface. To preserve this natural flow it should be clear to one skilled in the art that the cavity must be designed to prevent over accumulating emissions, while preventing the sample from being diluted by external air currents before it can be sampled and tested for emissions.

A gasket 45 can also be used to cover a portion of the low impedance cavity 37 to minimize the effect of external conditions that would disrupt or impact the atmosphere around the seal. Additionally, the gasket 45 can cover a portion of low impedance cavity to encourage a slight accumulation of emission in low impedance cavity 37. In another embodiment cover 28 can be utilized to cover a portion of low impedance cavity 37 and optimize accumulation and environmental effects on the emission sample.

Figure 3:
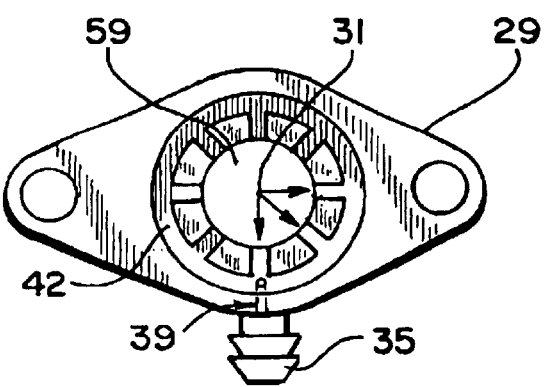
FIG. 3 depicts a top view of the base of the emission collection device depicted in FIG. 2.

A more detailed view of base 29 is illustrated in FIG. 3. Base 29 has a through hole 59 to allow for the insertion of a valve stem or in the case of a pump, a pump shaft. It should be appreciated to one skilled in the art that this hole 59 is sized to create the low impedance cavity to allow for the natural flow of emissions when it is fitted over the seal. In order to provide for a more uniform atmosphere sample from the low impedance cavity, the preferred embodiment includes multiple inlets 31 distributed proximate to and around the through hole 59. Orienting the inlets 31 to be perpendicular to rising emissions prevents unwanted samples from being trapped in a "pocket." A conduit 42 is provided to interconnect the inlets 31 to an outlet 39. A nipple 35 is fitted either between the base and the cover or in the cover or base to allow for the connection of the outlet 39 to an aspiration tube.

The inlets 31, conduit 42, and outlet 39 can be created in a number of ways. For example, recesses can be formed into the base, the cover, or both by milling, laser etching, plasma cutting, forging or molding. In order to provide for a uniform atmosphere sample around the seal, it is preferred that the inlets are designed to have the same orifice diameter when the cover and base are mated together to form conduit 42. It is also preferred that the conduit has an overall cross sectional area that is larger than the cumulative cross sectional area of each inlet. The purpose of this design is to provide an equal pressure drop across each inlet 31 during sample collection by a chemical detection system. An equal pressure drop will provide equal flow of the sample from the entire low impedance cavity and thus provide a uniform sample for emission analysis.

The foregoing has been a detailed description of preferred embodiments of this invention. Various modifications and additions can be made without departing from the spirit and scope of this invention. Accordingly, this description is meant to be taken only by way of example and not to otherwise limit the scope of the invention. For example the emission collection device can also be integrated with additional features to provide additional functionality. For instance, the valve ECD can perform as a retaining member for valve packing sets as illustrated in FIG. 2 or as an integral part of a flange. Other aspects, objects and advantages of the present invention can be obtained from a study of the drawings, the disclosure and the appended claims.

What is claims is:

1. A fugitive emission collection device comprising:
    a rigid member shaped to form a low impedance cavity that overlays a seal, the rigid member having a plurality of substantially equally spaced internal conduits defining discrete locations around an inside perimeter of the rigid member that are in fluid communication with the low impedance cavity for uniformly sampling atmosphere at the discrete locations proximate to the seal and an outlet in fluid communication with the plurality of internal conduits adapted for fluid communication with an emission detection system that can analyze the atmosphere to detect emissions leaking from the seal.

2. The emission collection device as in claim 1, wherein the rigid member secures a valve stem sealing assembly to a valve body.

3. The emission collection device as in claim 1, wherein the rigid member is further comprised of:
    a base having recesses formed along a mating surface; and
    a cover for attachment to the mating surface to create the conduit.

4. The emission collection device as in claim 3 further comprising a gasket for sealing the mating surface.

5. The emission collection device as in claim 3, wherein said conduit has a substantially circular portion and has radial feeds coupling the inlets to the substantially circular portion.

6. The emission collection device as in claim 1 further comprising a gasket for optimizing the impedance of the low impedance cavity by restricting air flow to and from the cavity.

7. The emission collection device as in claim 1 further comprising a gasket that optimizes the wind break capabilities and fugitive emission accumulation by creating impedance to air flow and emission flow.

8. The emission collection device as in claim 1, wherein said inlets each have equal cross sectional areas.

9. The emission collection device as in claim 1, further comprising a cover that optimizes the windbreak capabilities and fugitive emission accumulation by creating impedance to air flow and emission flow.

10. A fugitive emission collection device comprising:
    a rigid member shaped to form a low impedance cavity that overlays a seal, the rigid member comprising a base having recesses formed along a mating surface and a cover for attachment to the mating surface to create a conduit, the conduit having a plurality of substantially equally spaced inlets defining discrete locations around an inside perimeter of the rigid member in fluid communication with the low impedance cavity for uniformly sampling atmosphere at the discrete locations proximate the seal, and an outlet for fluid communication with an emission detection system that can analyze the atmosphere to detect emissions leaking from the seal.

11. The emission collection device as in claim 10 further comprising a gasket for sealing the mating surface.

12. The emission collection device as in claim 10, wherein said conduit has a substantially circular portion and has radial feeds coupling the inlets to the substantially circular portion.

13. The emission collection device as in claim 12, wherein said inlets each have equal cross sectional areas.

14. The emission collection device as in claim 10 further comprising a gasket that optimizes the wind break capabilities and fugitive emission accumulation by creating impedance to air flow and emission flow.

15. A fugitive emission collection device comprising:
    a rigid member shaped to form a low impedance cavity that overlays a seal, the rigid member having a substantially circular portion to form a conduit with a plurality of substantially equally spaced radial inlets defining discrete locations around an inside perimeter of the rigid member that are in fluid communication with the low impedance cavity for uniformly sampling atmosphere at the discrete locations proximate the seal, and an outlet for fluid communication with an emission detection system that can analyze the atmosphere to detect emissions leaking from the seal.

16. The emission collection device as in claim 15, wherein said inlets each have equal cross sectional areas.

17. The emission collection device as in claim 15, wherein the inlets and the conduit are sized such that a uniform sample of the atmosphere around the seal can be drawn by a chemical detection system.

* * * * *

UNITED STATES PATENT AND TRADEMARK OFFICE
CERTIFICATE OF CORRECTION

PATENT NO. : 6,796,324 B2
DATED : September 28, 2004
INVENTOR(S) : John P. Dilger et al.

It is certified that error appears in the above-identified patent and that said Letters Patent is hereby corrected as shown below:

Column 2,
Line 11, please delete "manufacturing" and insert -- manufacturing. --.
Line 57, please delete "due obstructions" and insert -- due to obstructions --.

Column 3,
Lines 34-35, please delete "a emission detection system" and insert -- an emission detection system --.

Column 4,
Line 27, please delete "system" and insert -- system. --.

Column 5,
Line 44, please delete "What is claims is:" and insert -- What is claimed is: --.

Signed and Sealed this

Twenty-ninth Day of March, 2005

JON W. DUDAS
*Director of the United States Patent and Trademark Office*